(12) United States Patent
King

(10) Patent No.: US 10,368,970 B2
(45) Date of Patent: Aug. 6, 2019

(54) DEVICE, SYSTEM, AND METHOD FOR NON-INVASIVE STERILIZATION OF MAMMALS AND OTHER ANIMALS

(71) Applicant: Randy L. King, Laurel, MD (US)

(72) Inventor: Randy L. King, Laurel, MD (US)

( * ) Notice: Subject to any disclaimer, the term of this patent is extended or adjusted under 35 U.S.C. 154(b) by 0 days.

(21) Appl. No.: 14/696,901

(22) Filed: Apr. 27, 2015

(65) Prior Publication Data

US 2015/0320533 A1    Nov. 12, 2015

Related U.S. Application Data

(60) Provisional application No. 61/989,036, filed on May 6, 2014.

(51) Int. Cl.
*A61N 7/02* (2006.01)
*A61D 1/06* (2006.01)
(Continued)

(52) U.S. Cl.
CPC ............... *A61D 1/06* (2013.01); *A61B 8/08* (2013.01); *A61B 8/4444* (2013.01); *A61B 8/4483* (2013.01); *A61B 8/461* (2013.01); *A61B 8/5207* (2013.01); *A61B 8/54* (2013.01); *A61N 7/02* (2013.01); *A61B 2018/00559* (2013.01); *A61B 2018/00577* (2013.01); *A61B 2090/378* (2016.02); *A61B 2503/40* (2013.01); *A61N 2007/0078* (2013.01)

(58) Field of Classification Search
CPC .............................................. A61N 2007/0052
See application file for complete search history.

(56) References Cited

U.S. PATENT DOCUMENTS 4,073,289 A *  2/1978  Fahim ...................... A61D 1/06
                                                              128/842
4,620,546 A *  11/1986  Aida ....................... G01S 15/899
                                                              600/439

(Continued)

OTHER PUBLICATIONS

Notification of Transmittal of the International Search Report and the Written Opinion of the International Searching Authority, or the Declaration dated Jul. 22, 2015 in connection with International Patent Application No. PCT/US2015/027742.

(Continued)

*Primary Examiner* — Luther Behringer

(57) ABSTRACT

An apparatus includes at least one transducer configured to (i) generate first ultrasonic signals and receive reflected first ultrasonic signals and (ii) generate second ultrasonic signals. The apparatus also includes a diagnostic ultrasound system configured to control generation of the first ultrasonic signals and to perform image processing using the reflected first ultrasonic signals in order to generate real-time images of tissue in an animal. The apparatus further includes a therapeutic ultrasound system configured to control generation of the second ultrasonic signals in order to ablate targeted tissue in the animal and sterilize the animal. The at least one transducer could include (i) a diagnostic transducer configured to generate the first ultrasonic signals and receive the reflected first ultrasonic signals and (ii) a therapeutic transducer configured to generate the second ultrasonic signals. A portable handheld housing could contain the at least one transducer.

20 Claims, 3 Drawing Sheets

(51) Int. Cl.
*A61B 8/08* (2006.01)
*A61B 8/00* (2006.01)
*A61B 18/00* (2006.01)
*A61N 7/00* (2006.01)
*A61B 90/00* (2016.01)

(56) References Cited

U.S. PATENT DOCUMENTS

| | | | | |
|---|---|---|---|---|
| 4,622,972 | A * | 11/1986 | Giebeler, Jr. | A61N 5/02 367/138 |
| 5,640,960 | A * | 6/1997 | Jones | A61B 8/0866 600/453 |
| 6,599,256 | B1 | 7/2003 | Acker et al. | |
| 6,852,082 | B2 | 2/2005 | Strickberger et al. | |
| 10,058,284 | B2 * | 8/2018 | Hoseit | A61B 5/6847 |
| 2002/0067359 | A1 * | 6/2002 | Brodsky | A61B 8/546 345/440 |
| 2003/0036705 | A1 * | 2/2003 | Hare | A61B 17/22012 600/437 |
| 2007/0213616 | A1 * | 9/2007 | Anderson | A61B 8/0833 600/448 |
| 2008/0114255 | A1 * | 5/2008 | Schwartz | A61B 8/00 600/474 |
| 2010/0016726 | A1 * | 1/2010 | Meier | A61B 8/00 600/459 |
| 2012/0029353 | A1 * | 2/2012 | Slayton | A61N 7/02 600/439 |
| 2013/0096597 | A1 | 4/2013 | Anand et al. | |
| 2014/0180034 | A1 * | 6/2014 | Hoseit | A61B 5/6847 600/301 |

OTHER PUBLICATIONS

Hokland, et al., "MRI-Guided Focused Ultrasound: Methodology and Applications," IEEE Transactions on Medical Imaging, vol. 25, No. 6, Jun. 2006, p. 723-731.

"Principles of MR guided Focused Ultrasound Surgery (MRgFUS) ExAblate Technology," http://us.insightec.com/MRgFUS-Technology.html, 2015 InSightec, 4 pages.

"Do you suffer from uterine fibroids?," ExAblate 2000, InSightec, Pub 2-40012 Rev.1, 2 pages.

* cited by examiner

DEVICE, SYSTEM, AND METHOD FOR NON-INVASIVE STERILIZATION OF MAMMALS AND OTHER ANIMALS

PRIORITY CLAIM

This application claims priority under 35 U.S.C. § 119(e) to U.S. Provisional Patent Application Ser. No. 61/989,036 filed on May 6, 2014. This provisional patent application is hereby incorporated by reference in its entirety.

TECHNICAL FIELD

This disclosure is generally directed to sterilization devices. More specifically, this disclosure is directed to a device, system, and method for the non-invasive sterilization of mammals and other animals.

BACKGROUND

The sterilization of animals is often a time-consuming process. In a conventional sterilization procedure, an animal is first sedated, and one or more incisions are formed in tissue of the animal using a scalpel. Once the sterilization procedure is completed, the animal often needs to wear an Elizabethan collar (pet cone) or other device to prevent the animal from licking or biting sutures or bandages. These types of sterilization procedures typically have inherent risks, such as risks associated with sedation and infection.

SUMMARY

This disclosure provides a device, system, and method for the non-invasive sterilization of mammals and other animals.

In a first embodiment, an apparatus includes at least one transducer configured to (i) generate first ultrasonic signals and receive reflected first ultrasonic signals and (ii) generate second ultrasonic signals. The apparatus also includes a diagnostic ultrasound system configured to control generation of the first ultrasonic signals and to perform image processing using the reflected first ultrasonic signals in order to generate real-time images of tissue in an animal. The apparatus further includes a therapeutic ultrasound system configured to control generation of the second ultrasonic signals in order to ablate targeted tissue in the animal and sterilize the animal.

In a second embodiment, a system includes at least one transducer configured to (i) generate first ultrasonic signals and receive reflected first ultrasonic signals and (ii) generate second ultrasonic signals. The system also includes a diagnostic ultrasound system configured to control generation of the first ultrasonic signals and to perform image processing using the reflected first ultrasonic signals in order to generate real-time images of tissue in an animal. The system further includes a therapeutic ultrasound system configured to control generation of the second ultrasonic signals in order to ablate targeted tissue in the animal and sterilize the animal. In addition, the system includes a display configured to present the real-time images to a user in order to allow the user to aim the at least one transducer at the targeted tissue.

In a third embodiment, a method includes generating real-time images of tissue in an animal using a diagnostic ultrasound system and at least one transducer. The method also includes ablating targeted tissue in the animal in order to sterilize the animal using a therapeutic ultrasound system and the at least one transducer. The at least one transducer is configured to generate first ultrasonic signals and receive reflected first ultrasonic signals, where the real-time images are generated using the reflected first ultrasonic signals. The at least one transducer is also configured to generate second ultrasonic signals, where the targeted tissue is ablated using the second ultrasonic signals.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 4, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
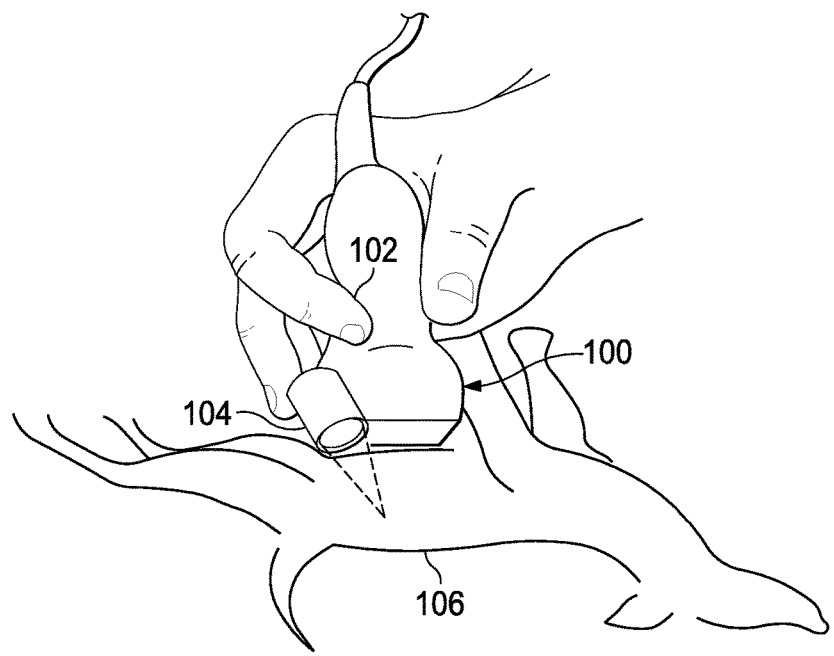
FIG. 1 illustrates an example device used for the sterilization of animals in accordance with this disclosure.

FIG. 1 illustrates an example device 100 used for the sterilization of animals in accordance with this disclosure. The device 100 represents a hand-held real-time instrument that can be used to sterilize mammals or other animals. As can be seen here, FIG. 1 is not drawn to scale.

As shown in FIG. 1, the device 100 includes a diagnostic transducer 102 and a therapeutic transducer 104 that are used to non-invasively sterilize a mammal or other animal 106. The animal 106 is shown here as being a dog, although the device 100 could be used to sterilize any other suitable animals. In general, the diagnostic transducer 102 is used to identify internal tissue within the animal 106 and to aim the therapeutic transducer 104, and the therapeutic transducer 104 is used to ablate targeted internal tissue within the animal 106.

By properly aiming the therapeutic transducer 104, the animal 106 can be spayed, neutered, or otherwise sterilized without requiring incisions in the animal 106. In this way, there may be little or no need to form incisions in the animal 106 being sterilized. Moreover, no sedation or light sedation could be used on the animal 106 being sterilized, rather than the heavier sedation typically utilized. In addition, there may be no need for the use of an Elizabethan collar or other device after the sterilization procedure, and this approach can eliminate any need for a follow-up visit. This approach therefore helps to reduce or even eliminate many of the risks associated with conventional sterilization procedures.

The diagnostic transducer 102 includes any suitable structure for identifying tissue to be ablated using ultrasound, such as a lower-power ultrasonic transducer. In some embodiments, the diagnostic transducer 102 could represent a multi-element piezoelectric structure, such as a multi-element lead zirconate titanate (PZT) or PZT composite ultrasonic transducer. The diagnostic transducer 102 could also operate at any suitable frequency or frequencies, such as between about 1 MHZ and about 10 MHz. The therapeutic transducer 104 includes any suitable structure for ablating tissue using ultrasound, such as a higher-power ultrasonic transducer. In some embodiments, the therapeutic transducer 104 could represent a single-element or multi-element piezoelectric structure, such as a single-element or multi-element PZT or PZT composite ultrasonic transducer. The therapeutic transducer 104 could also operate at any suitable frequency or frequencies, such as between about 0.5 MHZ and about 10 MHz.

Note that the diagnostic and therapeutic transducers 102-104 could represent separate devices, such as transducers mechanically coupled together to allow for imaging and therapy (ablation). The diagnostic and therapeutic transducers 102-104 could also be combined into a single structure, such as a combined array with one portion for imaging and another portion for therapy or a single array with common portions for imaging and therapy.

While not shown, the diagnostic transducer 102 and the therapeutic transducer 104 could be placed within a common housing or other structure. The housing or other structure could hold the transducers 102-104 in a known configuration or in known positions so that the diagnostic transducer 102 can be used to aim the therapeutic transducer 104. The housing could be formed from any suitable material(s), such as metal or plastic.

Although FIG. 1 illustrates one example of a device used for the sterilization of animals, various changes may be made to FIG. 1. For example, the device could include multiple diagnostic transducers 102 and/or multiple therapeutic transducers 104. Also, the form factors of the diagnostic and therapeutic transducers 102-104 and the form factor of the overall device 100 shown in FIG. 1 are for illustration only.

Figure 2:
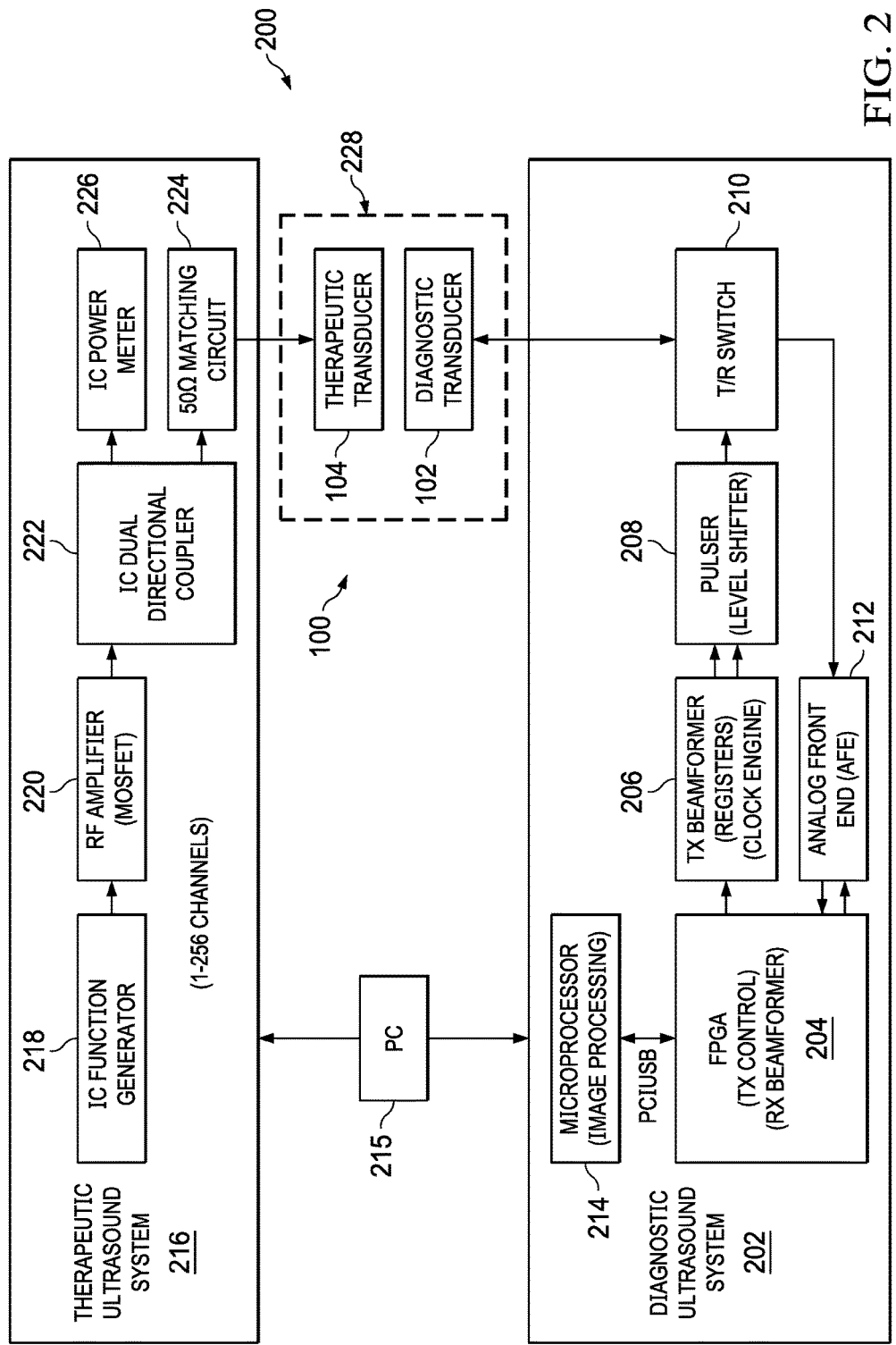
FIG. 2 illustrates an example system used for the sterilization of animals in accordance with this disclosure.

FIG. 2 illustrates an example system 200 used for the sterilization of animals in accordance with this disclosure. As shown in FIG. 2, the system 200 includes the device 100 described above with respect to FIG. 1. The system 200 also includes a diagnostic ultrasound system 202, which is used in conjunction with the diagnostic transducer 102. The diagnostic ultrasound system 202 controls ultrasonic signals transmitted by the diagnostic transducer 102 and processes ultrasonic signals received by the diagnostic transducer 102 in order to generate real-time images of the tissue of an animal 106.

The diagnostic ultrasound system 202 here includes a field programmable gate array (FPGA) 204 that (i) generates signals used to drive the diagnostic transducer 102 and (ii) processes incoming signals received from the diagnostic transducer 102. For example, the FPGA 204 can perform transmit (TX) control functions to control the ultrasonic signals generated by the diagnostic transducer 102. The FPGA 204 can also perform receive (RX) beamformer functions to process incoming signals reflected from tissue and other structures within an animal 106. The FPGA 204 includes any suitable structure supporting transmit control and receive processing. Note that an FPGA is one example of a device that could be used and that any other suitable processing or control device(s) (such as at least one microprocessor, microcontroller, DSP, or ASIC) could be used in place of the FPGA 204.

A transmit beamformer 206 performs functions for converting signals from the FPGA 204 into ultrasonic signals sent in desired direction(s) from the diagnostic transducer 102. The transmit beamformer 206 includes any suitable structure supporting beamforming, such as one or more registers and a clock engine. The output of the transmit beamformer 206 is used by a pulser 208 to generate pulse signals, which are sent to the diagnostic transducer 102 via a transmit/receive (T/R) switch 210. The pulser 208 converts signals from the transmit beamformer 206 into pulses that are then converted by the diagnostic transducer 102 into ultrasonic signals. The pulser 208 includes any suitable structure for generating pulses that create ultrasonic signals.

Incoming signals from the diagnostic transducer 102 are provided via the T/R switch 210 to an analog front end (AFE) 212, which processes and converts analog signals to generate digital information. The AFE 212 includes any suitable structure for receiving and processing analog signals, such as one or more filters, amplifiers, and analog-to-digital converters.

The incoming digital data is provided from the AFE 212 to a microprocessor 214 via the FPGA 204. The microprocessor 214 performs various functions associated with the sterilization of animals, such as image processing. As a particular example, the microprocessor 214 could output images obtained using the diagnostic transducer 102 for review by a user, such as via a personal computer (PC) or other computing device 215. These images can be used by the user to aim the diagnostic transducer 102 (and thereby aim the therapeutic transducer 104). The microprocessor 214 includes any suitable processing device, such as a single processor, a multi-core processor, or multiple homogenous or heterogeneous processing devices. Note that a microprocessor 214 is one example of a device that could be used and that any other suitable processing or control device(s) (such as at least one microcontroller, DSP, FPGA, or ASIC) could be used in place of the microprocessor 214.

In some embodiments, the diagnostic ultrasound system 202 could represent a conventional diagnostic ultrasound system provided by various manufacturers. In other embodiments, the diagnostic ultrasound system 202 could be customized, such as for a particular application.

As shown in FIG. 2, a therapeutic ultrasound system 216 is used in conjunction with the therapeutic transducer 104. The therapeutic ultrasound system 216 can include one or multiple channels, such as between one and 256 channels. In this example, each channel includes a function generator 218, an amplifier 220, a dual directional coupler 222, an impedance matching circuit 224, and a power meter 226.

The function generator 218 generates a signal that is amplified by the amplifier 220. For example, the function generator 218 could sweep a range of driving frequencies and create a sine wave at the appropriate fundamental frequency. The directional coupler 222 provides the bulk of the amplified signal to the impedance matching circuit 224, which provides the signal to the therapeutic transducer 104 for delivery to an animal 106 as ablative ultrasonic signals. A portion of the amplified signal is provided from the directional coupler 222 to the power meter 226, which can measure the current power of the amplified signal. This allows, for example, the user to alter operation of the therapeutic ultrasound system 216 so that signals having a desired amount of power are delivered to tissue of an animal 106 being sterilized.

The function generator 218 includes any suitable structure for generating signals to be amplified and output as ultrasonic signals. For example, the function generator 218 could be implemented using one or more integrated circuits (ICs). The amplifier 220 includes any suitable structure for amplifying signals, such as one or more MOSFET transistors forming a radio frequency (RF) amplifier. The dual directional coupler 222 includes any suitable structure for coupling RF or other signals to multiple destinations, such as one or more ICs. The impedance matching circuit 224 includes any suitable structure for matching the impedance of a signal line or other structure. In this example, the impedance matching circuit 224 is a 50Ω matching circuit, although other impedances could also be used. The power meter 226 includes any suitable structure for measuring the power of a signal (or portion thereof).

The computing device 215 represents a computer or other device that displays information associated with the device 100 or the ultrasound systems 202, 216 and that can be used to control the device 100 or the ultrasound systems 202, 216. For example, the computing device 215 could include a display, where real-time images generated by the diagnostic ultrasound system 202 using the diagnostic transducer 102 are presented on the display. The computing device 215 could also include one or more processing devices that execute one or more applications for processing or creating the real-time images for presentation on the display. The processing devices could also execute one or more applications for controlling the transducers 102-104 or the ultrasound systems 202, 216 based on user input. As a particular example, the processing devices could execute an application that can control the diagnostic transducer 102/diagnostic ultrasound system 202 and, when a user indicates that the diagnostic transducer 102 is suitably aimed, control the therapeutic transducer 104/therapeutic ultrasound system 216 to deliver suitable energy to sterilize an animal 106. The computing device 215 includes any suitable computing device or other device configured to display images and control a sterilization device.

The sterilization device 100 here includes a housing 228, which encases, supports, or otherwise contains the transducers 102-104 and optionally other components of the system 200. In this example, the housing 228 contains the transducers 102-104, and one or more cables could couple the housing 228 to the ultrasound systems 202, 216. However, this is for illustration only, and other embodiments of the system 200 could be used. For example, one or both ultrasound systems 202, 216 could reside within the housing 228. As another example, one ultrasound system could be contained within the housing 228, while another ultrasound system could reside outside the housing 228. In general, a wide variety of configurations could be used in terms of housing the components of the device 100 and the system 200, as long as the therapeutic transducer 104 can be aimed using the diagnostic transducer 102.

As noted above, the personal computer or other computing device 215 can be used here to support various functions. For example, images from the diagnostic ultrasound system 202 can be displayed on a monitor of the computing device 215. Also, the computing device 215 could be used to display other information associated with operation of the hand-held device 100. The other information could include current operating characteristics of the hand-held device 100 (such as measurements from the power meter 226) and settings for the hand-held device 100 (such as a desired power level of the ultrasonic signals from the therapeutic transducer 104). Any suitable interface could be used to couple the computing device 215 to the ultrasound systems 202, 216.

In some embodiments, the diagnostic transducer 102 and the diagnostic ultrasound system 202 are used to capture images inside an animal 106 to be sterilized and aim the therapeutic transducer 104. Once aimed properly, the therapeutic ultrasound system 216 and the therapeutic transducer 104 are used to direct ablative ultrasound signals to the desired location(s) of the animal 106 in order to sterilize the animal. Note that the therapeutic transducer 104 could be geometrically, electronically, or otherwise focused and have a specified diameter and focal length, which are characteristics that can be used to determine specifically where ultrasound signals from the therapeutic transducer 104 will ablate the animal's tissue. Once an ablation of tissue has completed, the diagnostic transducer 102 and the diagnostic ultrasound system 202 can again be used to verify whether the necessary or desired ablations have occurred, and if necessary further ablations can occur. This supports real-time feedback to the user so that the user can view the actual ablations caused by the therapeutic transducer 104 using images generated using the diagnostic transducer 102.

Although FIG. 2 illustrates one example of a system 200 used for the sterilization of animals, various changes may be made to FIG. 2. For example, the functional division shown in FIG. 2 is for illustration only. Various components and groups of components in FIG. 2 could be combined, further subdivided, rearranged, or omitted and additional components could be added according to particular needs. As a particular example, the transducers 102-104 could be partially or completely combined, such as by using a single transducer array. As another example, the functionality of the microprocessor 214 or other portions of the ultrasound system(s) 202, 216 could be implemented within the computing device 215 or within the device 100.

Figure 3:
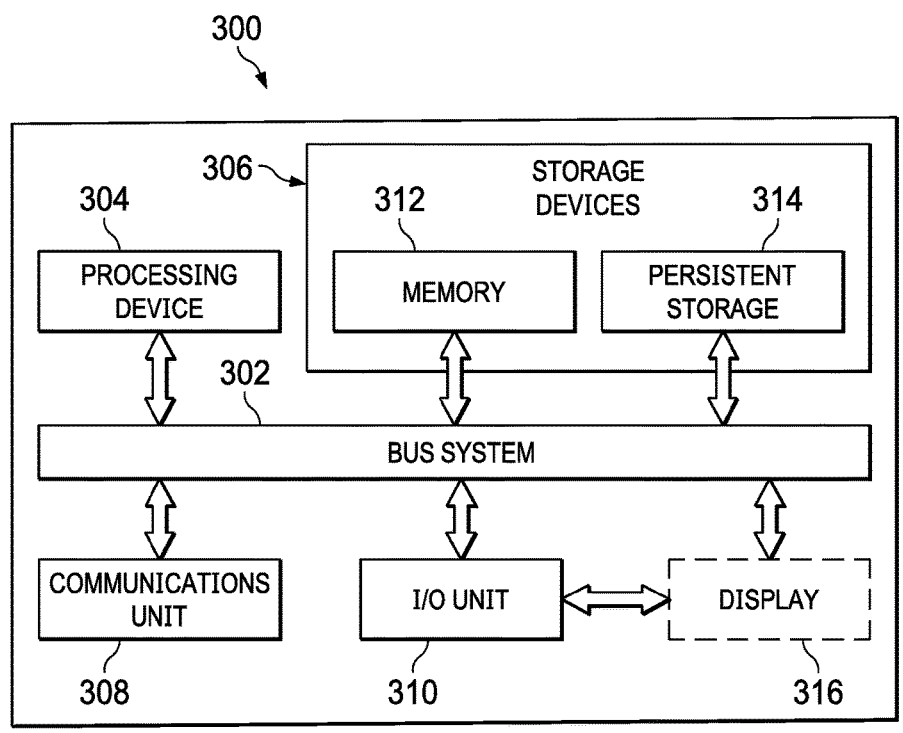
FIG. 3 illustrates an example computing device used for the sterilization of animals in accordance with this disclosure.

FIG. 3 illustrates an example computing device 300 used with a sterilization device in accordance with this disclosure. The device 300 could, for example, be used to implement the computing device 215 that operates in conjunction with the sterilization device 100 of FIG. 1.

As shown in FIG. 3, the device 300 includes a bus system 302, which supports communication between at least one processing device 304, at least one storage device 306, at least one communications unit 308, and at least one input/output (I/O) unit 310. The processing device 304 executes instructions that may be loaded into a memory 312. The processing device 304 may include any suitable number(s) and type(s) of processors or other devices in any suitable arrangement. Example types of processing devices 304 include microprocessors, microcontrollers, DSPs, FPGAs, ASICs, and discrete circuitry.

The memory 312 and a persistent storage 314 are examples of storage devices 306, which represent any structure(s) capable of storing and facilitating retrieval of information (such as data, program code, and/or other suitable information on a temporary or permanent basis). The memory 312 may represent a random access memory or any other suitable volatile or non-volatile storage device(s). The persistent storage 314 may contain one or more components or devices supporting longer-term storage of data, such as a ready only memory, hard drive, Flash memory, or optical disc.

The communications unit 308 supports communications with other systems or devices. For example, the communications unit 308 could include a network interface that facilitates communications over at least one Ethernet, HART, FOUNDATION Fieldbus, or other network. The communications unit 308 could also include a wireless transceiver facilitating communications over at least one wireless network. The communications unit 308 may support communications through any suitable physical or wireless communication link(s).

The I/O unit 310 allows for input and output of data. For example, the I/O unit 310 may provide a connection for user input through a keyboard, mouse, keypad, touchscreen, or other suitable input device. The I/O unit 310 may also send output to a display, printer, or other suitable output device. In this example, a display 316 may form an integral part of the computing device 300, although the display 316 could also be external to the computing device 300 and driven using the I/O unit 310.

Although FIG. 3 illustrates one example of a computing device 300 used with a sterilization device, various changes may be made to FIG. 3. For example, various components in FIG. 3 could be combined, further subdivided, or omitted and additional components could be added according to particular needs. Also, computing devices can come in a wide variety of configurations, and FIG. 3 does not limit this disclosure to any particular configuration of computing device.

Figure 4:
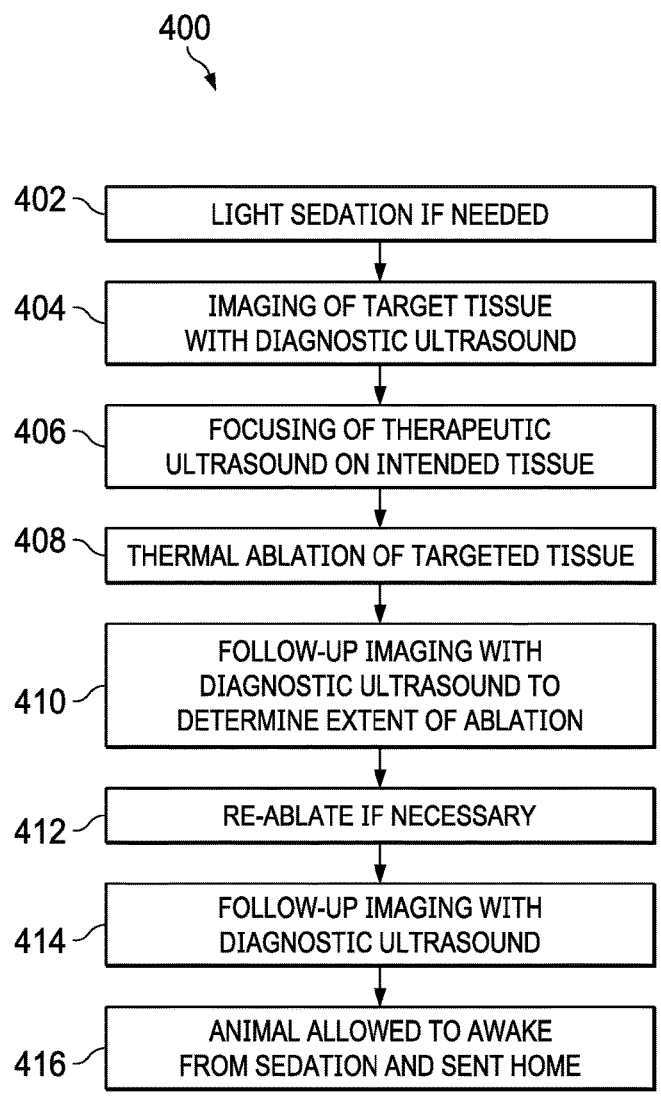
FIG. 4 illustrates an example method for the sterilization of animals in accordance with this disclosure.

FIG. 4 illustrates an example method 400 for the sterilization of animals in accordance with this disclosure. For ease of explanation, the method 400 is described with respect to the sterilization device 100 shown in FIG. 1 and the system 200 shown in FIG. 2. However, the method 400 could be used with any other suitable sterilization device and system.

As shown in FIG. 4, an animal may optionally be lightly sedated for the sterilization procedure at step 402. Note that sedation may not be needed, such as for calmer animals 106. Also note that heavier sedation or full unconscious anesthesia may not be necessary, although nothing prevents such heavier sedation or unconscious anesthesia from being used. Once sedated or ready, the animal 106 can be placed into an appropriate position, such as on its back.

Imaging of target tissue to be ablated occurs using diagnostic ultrasound at step 404. For example, an ultrasound imaging examination can take place to locate the target tissue to be ablated. This ultrasound imaging examination can include the diagnostic ultrasound system 202 generating signals that cause the diagnostic transducer 102 to produce ultrasonic signals in the animal 106. This could also include the diagnostic ultrasound system 202 receiving reflected signals via the diagnostic transducer 102 and processing the signals to generate real-time images, which can be presented on the computing device 215.

Once located, therapeutic ultrasound is focused onto the target tissue to be ablated at step 406. The focusing could occur in any suitable manner. For example, the therapeutic transducer 104 could be physically moved to align with the target tissue, where the target tissue is identified using the diagnostic transducer 102. As another example, the therapeutic transducer 104 could be electronically focusing onto an intended portion of the target tissue, where the target tissue is identified using the diagnostic transducer 102.

Thermal ablation of the target tissue can then begin at step 408. The thermal ablation could include the therapeutic ultrasound system 216 generating signals that cause the therapeutic transducer 104 to produce ablative ultrasonic signals in the animal 106. The power and duration of the therapy depend on various factors, such as the size of the animal 106, the depth of the tissue being ablated, and the fat content of the surrounding tissue. A focused therapeutic transducer 104 of the highest frequency possible could be used to limit far field damage to untargeted tissue.

Diagnostic imaging after the therapy can be done to help determine the extent of tissue ablation at step 410. This could include using the diagnostic ultrasound equipment to generate additional images of the animal's tissue. If needed, re-ablation of target tissue could be repeated one or more times at step 412, and each ablation can be followed by diagnostic imaging at step 414 to help determine the extent of the ablation.

Once adequate tissue has been ablated, the animal can be awakened (if sedated) and sent home at step 416. If successful, no further treatment may be necessary. Otherwise, a follow-up treatment could be performed, such as in the same manner shown in FIG. 4.

With the procedure shown in FIG. 4, there is no risk of infection as the procedure is non-invasive. There would also be no need to send the animal home with an Elizabethan collar because there are no sutures or bandages. Further, the procedure could be totally painless, but mild pain relievers may be prescribed to make the animal more comfortable. It may also be recommended that the animal not be too active for a period of time, such as 24 hours, in case of internal bleeding.

Although FIG. 4 illustrates one example of a method 400 for the sterilization of animals, various changes may be made to FIG. 4. For example, while shown as a series of steps, various steps in FIG. 4 could overlap, occur in parallel, occur multiple times, or occur in a different order. As a particular example, if appropriate frequencies are selected, diagnostic imaging could overlap with therapeutic treatment, allowing real-time images of the animal's tissue to be viewed during the therapeutic treatment (and possibly allowing a user to view changes to the animal's tissue in real-time). Also, various steps in FIG. 4 could be omitted, such as when only one ablation step is needed.

In some embodiments, various functions described in this patent document are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "at least one of," when used with a list of items, means that different combinations of one or more of the listed items may be used, and only one item in the list may be needed. For example, "at least one of A, B, and C" includes any of the following combinations: A, B, C, A and B, A and C, B and C, and A and B and C. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A handheld apparatus comprising:
at least one first transducer configured to generate first ultrasonic signals and receive reflected first ultrasonic signals;
at least one second transducer configured to generate second ultrasonic signals;
a diagnostic ultrasound system configured to control generation of the first ultrasonic signals and to perform image processing using the reflected first ultrasonic signals in order to generate real-time images of tissue in an animal, wherein the diagnostic ultrasound system comprises:
a transmit/receive (T/R) switch coupled to a pulser, the at least one first transducer, and an analog front end, the pulser comprising a level shifter and coupled to the T/R switch, the analog front end comprising one or more filters, one or more amplifiers, and one or more analog-to-digital converters,
a transmit (TX) beamformer comprising one or more registers and a clock engine and coupled to the pulser, and
a processing device comprising a microprocessor, microcontroller, field programmable gate array (FPGA), digital signal processor (DSP), or application specific integrated circuit (ASIC) coupled to the TX beamformer, the analog front end, and a second processing device configured to perform image processing and generate the real-time images;
a therapeutic ultrasound system configured to control generation of the second ultrasonic signals in order to ablate targeted tissue in the animal and sterilize the animal, wherein the therapeutic ultrasound system comprises:
a function generator configured to generate a therapeutic signal,
an amplifier configured to amplify the therapeutic signal,
a directional circuit configured to provide a first portion of the therapeutic signal to an electrical impedance matching circuit and a second portion of the therapeutic signal to a power meter, the electrical impedance matching circuit configured to provide the first portion of the therapeutic signal to the at least one second transducer for the second ultrasonic signals, the power meter configured to measure a current power of the amplified therapeutic signal; and
a portable housing that contains the at least one first transducer, the at least one second transducer, the therapeutic ultrasound system, and the diagnostic ultrasound system including the T/R switch, the pulser, the analog front end, the TX beamformer, and the processing device.

2. The handheld apparatus of claim 1, wherein:
the at least one first transducer comprises a diagnostic transducer configured to generate the first ultrasonic signals and receive the reflected first ultrasonic signals; and
the at least one second transducer comprises a therapeutic transducer configured to generate the second ultrasonic signals.

3. The handheld apparatus of claim 2, wherein the first and second transducers are arranged such that the therapeutic transducer is configured to be aimed at the targeted tissue based on the real-time images.

4. The handheld apparatus of claim 2, wherein the therapeutic ultrasound system is configured to focus the second ultrasonic signals onto the targeted tissue.

5. The handheld apparatus of claim 1, wherein the diagnostic ultrasound system is configured to generate the real-time images of the tissue in the animal during generation of the second ultrasonic signals.

6. The handheld apparatus of claim 1, wherein the second processing device is configured to generate the real-time images during generation of the second ultrasonic signals such that the real-time images show changes to the targeted tissue during the ablation of the targeted tissue.

7. A system comprising:
a handheld apparatus comprising:
at least one first transducer configured to generate first ultrasonic signals and receive reflected first ultrasonic signals;
at least one second transducer configured to generate second ultrasonic signals;
a diagnostic ultrasound system configured to control generation of the first ultrasonic signals and to perform image processing using the reflected first ultrasonic signals in order to generate real-time images of tissue in an animal, wherein the diagnostic ultrasound system comprises:
a transmit/receive (T/R) switch coupled to a pulser, the at least one first transducer, and an analog front end, the pulser comprising a level shifter and coupled to the T/R switch, the analog front end comprising one or more filters, one or more amplifiers, and one or more analog-to-digital converters,
a transmit (TX) beamformer comprising one or more registers and a clock engine and coupled to the pulser, and
a processing device comprising a microprocessor, microcontroller, field programmable gate array (FPGA), digital signal processor (DSP), or application specific integrated circuit (ASIC) coupled to the TX beamformer, the analog front end, and a second processing device configured to perform image processing and generate the real-time images;
a therapeutic ultrasound system configured to control generation of the second ultrasonic signals in order to ablate targeted tissue in the animal and sterilize the animal, wherein the therapeutic ultrasound system comprises:
a function generator configured to generate a therapeutic signal,
an amplifier configured to amplify the therapeutic signal,
a directional circuit configured to provide a first portion of the therapeutic signal to an electrical impedance matching circuit and a second portion of the therapeutic signal to a power meter, the electrical impedance matching circuit configured to provide the first portion of the therapeutic signal to the at least one second transducer for the second ultrasonic signals, the power meter configured to measure a current power of the amplified therapeutic signal; and a portable housing that contains the at least one first transducer, the at least one second transducer, the therapeutic ultrasound system, and the diagnostic ultrasound system including the T/R switch, the pulser, the analog front end, the TX beamformer, and the processing device; and a display configured to present the real-time images to a user in order to allow the user to aim the at least one second transducer at the targeted tissue.

8. The system of claim 7, wherein:
the at least one first transducer comprises a diagnostic transducer configured to generate the first ultrasonic signals and receive the reflected first ultrasonic signals; and
the at least one second transducer comprises a therapeutic transducer configured to generate the second ultrasonic signals.

9. The system of claim 8, wherein the therapeutic ultrasound system is configured to focus the second ultrasonic signals onto the targeted tissue.

10. The system of claim 7, wherein the diagnostic ultrasound system is configured to generate the real-time images of the tissue in the animal during generation of the second ultrasonic signals.

11. The system of claim 7, further comprising:
a computing device configured to control the diagnostic ultrasound system and the therapeutic ultrasound system, the computing device including the display.

12. The system of claim 7, wherein the display is integrated in the handheld apparatus.

13. The system of claim 7, wherein the second processing device is configured to generate the real-time images during generation of the second ultrasonic signals such that the real-time images show changes to the targeted tissue during the ablation of the targeted tissue.

14. A method comprising:
generating real-time images of tissue in an animal using a diagnostic ultrasound system and at least one first transducer, wherein the diagnostic ultrasound system comprises:
a transmit/receive (T/R) switch coupled to a pulser, the at least one first transducer, and an analog front end, the pulser comprising a level shifter and coupled to the T/R switch, the analog front end comprising one or more filters, one or more amplifiers, and one or more analog-to-digital converters,
a transmit (TX) beamformer comprising one or more registers and a clock engine and coupled to the pulser, and
a processing device comprising a microprocessor, microcontroller, field programmable gate array (FPGA), digital signal processor (DSP), or application specific integrated circuit (ASIC) coupled to the TX beamformer, the analog front end, and a second processing device configured to perform image processing and generate the real-time images; and
ablating targeted tissue in the animal in order to sterilize the animal using a therapeutic ultrasound system and at least one second transducer, wherein the therapeutic ultrasound system comprises:
a function generator configured to generate a therapeutic signal,
an amplifier configured to amplify the therapeutic signal,
a directional circuit configured to provide a first portion of the therapeutic signal to an electrical impedance matching circuit and a second portion of the therapeutic signal to a power meter, the electrical impedance matching circuit configured to provide the first portion of the therapeutic signal to the at least one second transducer for second ultrasonic signals, the power meter configured to measure a current power of the amplified therapeutic signal;
wherein:
the at least one first transducer is configured to generate first ultrasonic signals and receive reflected first ultrasonic signals, the real-time images generated using the reflected first ultrasonic signals;
the at least one second transducer is configured to generate the second ultrasonic signals, the targeted tissue ablated using the second ultrasonic signals; and
the at least one first transducer, the at least one second transducer, the therapeutic ultrasound system, and the diagnostic ultrasound system including the T/R switch, the pulser, the analog front end, the TX beamformer, and the processing device are located in a portable housing of a handheld apparatus.

15. The method of claim 14, wherein:
the at least one first transducer comprises a diagnostic transducer;
generating the real-time images comprises using the diagnostic ultrasound system and the diagnostic transducer;
the at least one second transducer comprises a therapeutic transducer; and
ablating the targeted tissue comprises using the therapeutic ultrasound system and the therapeutic transducer.

16. The method of claim 15, further comprising:
aiming the therapeutic transducer at the targeted tissue based on the real-time images.

17. The method of claim 15, further comprising:
focusing the second ultrasonic signals onto the targeted tissue using the therapeutic ultrasound system.

18. The method of claim 14, wherein the real-time images of the tissue in the animal are generated during generation of the second ultrasonic signals.

19. The method of claim 18, wherein the real-time images show changes to the targeted tissue during the ablation of the targeted tissue.

20. The method of claim 14, wherein the second processing device generates the real-time images during generation of the second ultrasonic signals such that the real-time images show changes to the targeted tissue during the ablation of the targeted tissue.

* * * * *